(12) United States Patent
Magnusson (10) Patent No.: US 10,137,445 B2
(45) Date of Patent: Nov. 27, 2018

(54) SINGLE USE CAPILLARY MICROPIPETTE FOR DISPENSING A DEFINED VOLUME OF A LIQUID

(71) Applicant: Gunnar Magnusson, Årsta (SE)

(72) Inventor: Gunnar Magnusson, Årsta (SE)

(*) Notice: Subject to any disclaimer, the term of this patent is extended or adjusted under 35 U.S.C. 154(b) by 413 days.

(21) Appl. No.: 14/967,582

(22) Filed: Dec. 14, 2015

(65) Prior Publication Data

US 2016/0193601 A1 Jul. 7, 2016

Related U.S. Application Data (60) Provisional application No. 62/100,167, filed on Jan. 6, 2015, provisional application No. 62/127,471, filed on Mar. 3, 2015.

(51) Int. Cl.
*G01N 1/00* (2006.01)
*B01L 3/02* (2006.01)

(52) U.S. Cl.
CPC ......... *B01L 3/022* (2013.01); *B01L 2200/025* (2013.01); *B01L 2200/0684* (2013.01); *B01L 2200/141* (2013.01); *B01L 2300/0838* (2013.01); *B01L 2300/0854* (2013.01); *B01L 2300/161* (2013.01); *B01L 2400/0478* (2013.01)

(58) Field of Classification Search
CPC ............. B01L 3/02; B01L 3/021; B01L 3/022
See application file for complete search history.

(56) References Cited

U.S. PATENT DOCUMENTS

| 6,403,037 B1* | 6/2002 | Chang | B01L 3/502 250/238 |
| 2010/0326214 A1* | 12/2010 | Hornes | B01L 3/021 73/864.01 |
| 2016/0136637 A1* | 5/2016 | Leckebusch | B01L 3/0217 422/522 |

* cited by examiner

*Primary Examiner* — Jyoti Nagpaul
(74) *Attorney, Agent, or Firm* — CUSPA Technology Law Associates; Yi Li (57) ABSTRACT

A single use capillary micropipette and a method of use for dispensing a defined volume of a liquid are disclosed. The capillary micropipette includes a housing, a piston disposed therein and a capillary tube connected to the housing. The housing has a holding chamber including chamber snap fit elements on the chamber wall, piston stop(s) and a bottom having a central opening with a tubular member extending therefrom. The piston includes a push cap having snap fit arms extending downward and a piston rod. In the assembled position, a venting space between the piston head and the central opening permits venting during aspiration of a liquid into capillary tube by capillary force. In response to an applied downward force, the snap fit arms of the push cap snap over chamber snap fit elements and piston rod slides in the tubular member, thereby dispensing a defined volume of the liquid.

20 Claims, 7 Drawing Sheets

SINGLE USE CAPILLARY MICROPIPETTE FOR DISPENSING A DEFINED VOLUME OF A LIQUID

CROSS REFERENCE TO RELATED APPLICATION

This application claims the benefit under 35 U.S.C. 119 (e) of the provisional patent application No. 62/100,167 filed Jan. 6, 2015 and provisional patent application No. 62/127,471 filed Mar. 3, 2015, which are hereby incorporated by reference in their entirety.

FIELD OF THE INVENTION

The present invention relates to a liquid transfer and dispensing device, more specifically relates to a single use capillary micropipette for dispensing a defined volume of a biological sample.

BACKGROUND OF THE INVENTION

A liquid biological sample such as blood is typically taken from a patient using a fingerstick or withdrawn with a syringe or a sealed vacuum tube. The biological sample often needs to be transferred from an open site, such as a droplet formed from fingerstick or from an opened sample tube, for diagnostic analysis. Typically, a micro capillary tube or a simple blood transfer device is used for transferring and dispensing the biological sample. However, existing simple blood transfer devices utilizing capillary action have various deficiencies and are not convenient to use.

One commonly used device for delivering a specific volume of a blood sample is Aqua Cap™ manufactured by Drummond Scientific Inc. This device is a glass capillary tube with a liquid tight plunger, positioned half way in the glass tube. A blood sample is taken via capillary action to the position of the plunger. The blood sample is dispensed by pressing the plunger using a plunger rod that is inserted into the glass tube by the user. Due to the small dimension of the capillary tube, it is difficult for the user to insert the plunger rod into the capillary tube for each use. Moreover, the plunger rod can be easily entered from a wrong direction.

Another commonly used device is a glass capillary tube connected at one end to a reusable rubber bulb. The user needs to connect the rubber bulb to the glass capillary tube before use and remove the rubber bulb from the contaminated glass capillary tube after dispensing a sample. This device requires substantial skill of the user in order to deliver a desired amount of a sample. Moreover, manual disassembly of the contaminated glass capillary tube after each use exposes the user to a high risk of contamination by the biological samples.

Therefore, there is a need for an improved capillary micropipette that overcomes the above mentioned deficiencies.

SUMMARY OF THE INVENTION

In one aspect, the present invention is directed to a single use capillary micropipette for dispensing a defined volume of a liquid. In one embodiment, the capillary micropipette comprises a housing comprising an upper holding chamber having an open top, a chamber wall having at least one set of chamber snap fit elements on an inner side thereof, one or more piston stops, and a bottom with a central opening, and a tubular member extending downward from the central opening on the bottom of the upper holding chamber; a piston comprising a push cap disposed at least partially in the holding chamber, the push cap including a top pusher and at least one set of snap fit arms extending downward from an underside of the top pusher; each of the at least one set of snap fit arms comprising at least one hook complementary to corresponding chamber snap fit element; and in an assembled position of the capillary micropipette the at least one hook on each of the at least one set of snap fit arms being situated on top of corresponding chamber snap fit element, and a piston rod having a piston head at a distal end thereof, the piston rod extending downward from the underside of the top pusher, coaxial with the central opening on the bottom of the upper holding chamber and the tubular member; in the assembled position of the capillary micropipette, a venting space between the piston head and the central opening on the bottom of the upper holding chamber permitting air communication between the tubular member and atmosphere through the upper holding chamber; and a capillary tube having a proximal open end connected to the tubular member and an opposing distal open end; the capillary tube capable of aspirating a liquid through the distal open end by capillary action to the proximal open end thereof while the capillary micropipette permitting venting through the venting space during aspiration. The push cap is movable downward in response to a force applied thereon to an extent at which at least one part of the push cap abuts against the one or more piston stops of the upper holding chamber, and such a downward movement of the push cap causes the at least one hook on each of the snap fit arms of the push cap to irreversibly snap over corresponding chamber snap fit element and the piston head to slide in the tubular member in the absence of venting thereby resulting in dispensing a defined volume of the liquid aspirated in the capillary tube.

In a further aspect, the present invention is directed to a method of transferring a liquid and dispensing a defined volume of the liquid using the single use capillary micropipette of the present invention. In one embodiment, the method comprises providing a capillary micropipette of the present invention; immersing the distal open end of the capillary tube in the liquid, and allowing the liquid to be aspirated into the capillary tube by capillary action while the capillary micropipette permitting venting through the venting space during aspiration; removing the distal open end of the capillary tube from the liquid when the liquid is aspirated to the proximal open end of the capillary tube; and pressing on top of the push cap to cause the hooks of the at least one set of snap fit arms to irreversibly snap over the at least one set of chamber snap fit elements of the upper holding chamber and to move the push cap downward until the at least one part of the push cap abuts against the one or more piston stops in the upper holding chamber, thereby the piston head sliding in the tubular member in the absence of venting and resulting in dispensing a defined volume of the liquid aspirated in the capillary tube.

The advantages of the present invention will become apparent from the following description taken in conjunction with the accompanying drawings showing exemplary embodiments of the invention.

BRIEF DESCRIPTION OF THE DRAWINGS

It is noted that in the drawings like numerals refer to like components.

DETAILED DESCRIPTION OF THE INVENTION

Embodiments of the present invention generally relate to a single use capillary micropipette for aspirating a liquid from an open site and dispensing a defined volume of the liquid. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In some embodiments, the capillary micropipette comprises a housing, a piston disposed therein and a capillary tube connected to the housing. The housing comprises an upper holding chamber and a tubular member extending from the bottom of the upper holding chamber. The upper holding chamber includes an open top, a chamber wall having at least one set of chamber snap fit elements on the inner side thereof, one or more piston stops, and a bottom having a central opening. The piston includes a push cap disposed at least partially in the holding chamber and a piston rod. The push cap includes a top pusher and at least one set of snap fit arms extending downward from an underside of the top pusher. The piston rod extends downward from the underside of the top pusher, coaxial with the central opening on the bottom of the upper holding chamber and the tubular member, and has a piston head at a distal end thereof. The capillary tube is connected to the tubular member, and is capable of aspirating a liquid by capillary action.

Figure 1:
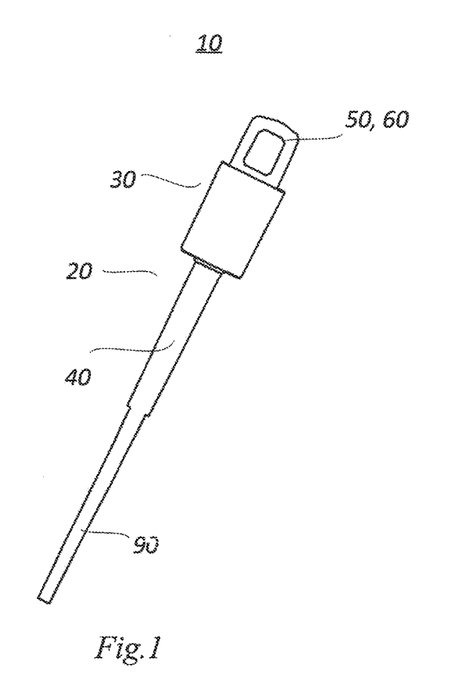
FIG. 1 is a side view of a capillary micropipette according to one embodiment of the present invention, which is tilted as usually seen for dispensing.
Figure 1A:
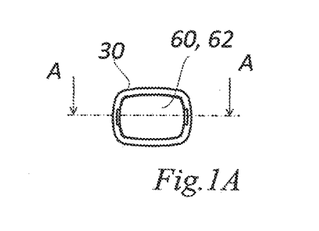
FIG. 1A is a top view of the capillary micropipette shown in FIG. 1.
Figures 3, 3A, 4, 4A, 5:
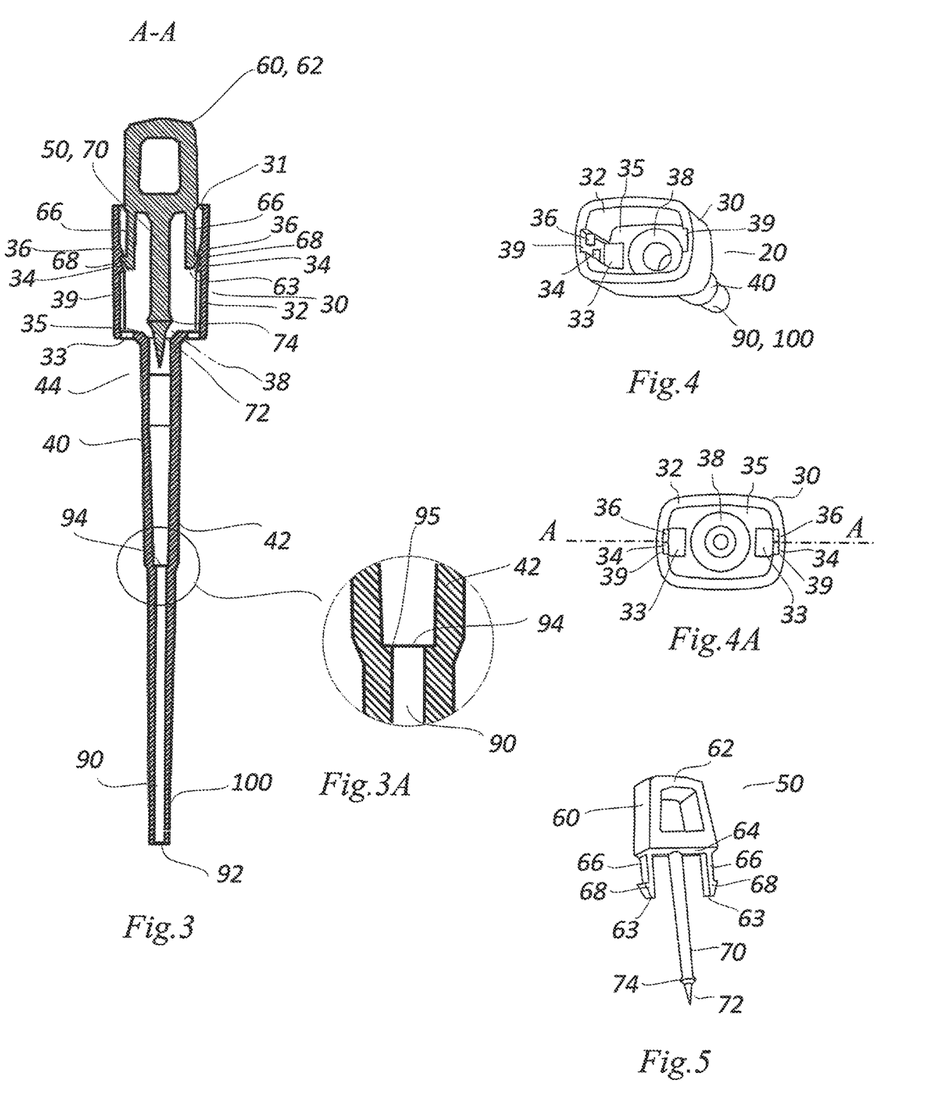
FIG. 3 is a cross sectional view of the capillary micropipette shown in FIG. 1, along line A-A in FIG. 1A, at an assembled position.
FIG. 3A is an enlarged partial cross sectional view showing the structure between the proximal open end of the capillary tube and distal segment of the tubular member of the capillary micropipette shown in FIG. 3.
FIG. 4 is a top perspective view and FIG. 4A is a top view, respectively, of the capillary micropipette shown in FIGS. 1 and 3, with the piston removed.
FIG. 5 is a perspective view of the piston of the capillary micropipette shown in FIGS. 1 and 3.

Referring now to the drawings, FIGS. 1 and 1A show a side and top view, respectively, of capillary micropipette 10 in one embodiment of the present invention. In FIG. 1, the capillary micropipette is tilted as typically seen at the time of dispensing a liquid. FIG. 3 shows a cross sectional view of the capillary micropipette, along line A-A in FIG. 1A. As shown, capillary micropipette 10 comprises a housing 20, a piston 50, and a capillary tube 90.

As shown in FIGS. 1, 3, 4 and 4A, housing 20 includes an upper holding chamber 30 and a tubular member 40 extending downward from upper holding chamber 30. The holding chamber 30 has an open top 31, a bottom 35 with a central opening 38 and a chamber wall 32. The chamber wall 32 includes at least one set of chamber latches on the inner side thereof, as the chamber snap fit elements, disposed along the inner circumference of the chamber wall for snap fit, or cantilever snap joint, with a push cap 60 of piston 50, as described below. In the embodiment shown in FIGS. 3, 4 and 4A, chamber wall 32 has a first or lower set of chamber latches 34 and a second or upper set of chamber latches 36 on the inner side of chamber wall 32. In the embodiment shown, both lower and upper sets of chamber latches 34 and 36 are in a pair form, disposed on opposing side of the upper holding chamber.

Figure 12:
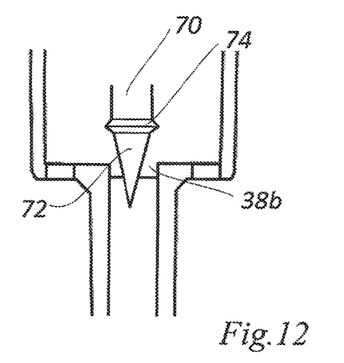
FIG. 12 is a partial cross sectional view of the capillary micropipette in an alternative embodiment of the present invention.

The tubular member 40 extends integrally downward from the central opening 38 on bottom 35 of upper holding chamber 30, and has a distal segment 42 and a proximal segment 44. In the embodiment shown in FIG. 3, central opening 38 tapers downward and has a general cone shape (see FIG. 9 also). Alternatively, the central opening can also be straight without tapering, such as central opening 38b in an alternative embodiment shown in FIG. 12

As illustrated in FIGS. 3 and 5, piston 50 includes a push cap 60 configured complementary to the interior of upper holding chamber 30 and disposed at least partially in the upper holding chamber, and a piston rod 70 with a piston head 72 at its distal end. The push cap 60 includes a top pusher 62, and at least one set of snap fit arms 66 extending downward from an underside or lower surface 64 of the top pusher. In the embodiment shown, snap fit arms 66 are cantilever snap fit arms. Each cantilever snap fit arm 66 includes at least one hook 68 complementary to corresponding chamber latch 34, 36 for snap fit or snap joining with the chamber latches on the corresponding side of the upper holding chamber. The height of the hooks is complementary to the distance between lower and upper sets of chamber latches 34 and 36.

In an assembled capillary micropipette 10 as shown in FIG. 3, hooks 68 on the cantilever snap fit arms 66 are disposed between the lower and upper sets of chamber latches 34 and 36. At this assembled position, hooks 68 are already irreversibly snapped over or snap-joint with the upper set chamber latches 36. Once assembled, the upper set chamber latches 36 prohibits the push cap from being removed from upper holding chamber 30. On the other hand, at this assembled position, hooks 68 are situated on top of, and not snapped over, the lower set chamber latches 34. The lower set chamber latches 34 inhibit piston rod 70 from moving downward, in the absence of a force specifically applied on the push cap. Hooks 68 snapping over the lower set chamber latches 34, also referred to as snap joint engagement between hooks 68 and the lower set chamber latches 34, occurs during the use of the device in dispensing a liquid as described hereinafter. In the embodiment shown, the chamber latches are in the form of protruding elements to engage with the hooks of the cantilever snap fit arms. Alternatively, the chamber latches may also be in a form of recess on the chamber wall to engage with the hooks of the cantilever snap fit arms through snap fit mechanism.

Figure 6:
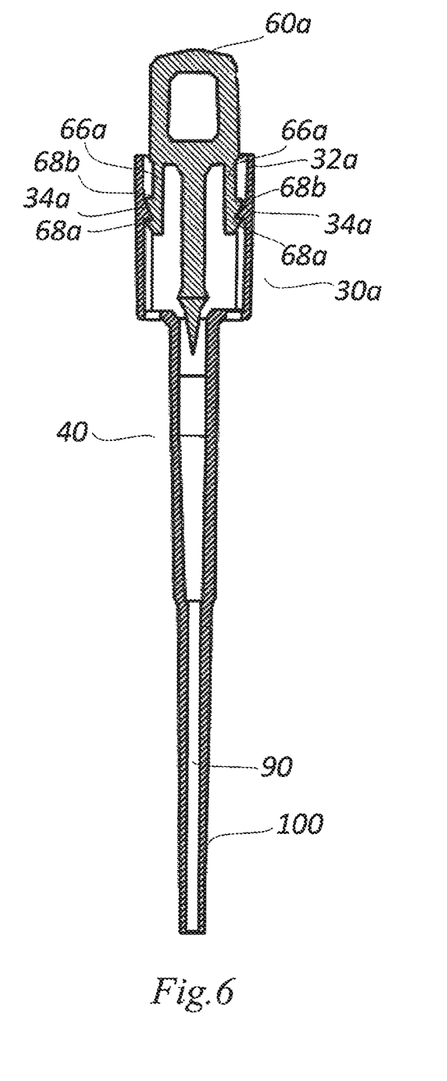
FIG. 6 is a cross sectional view of the capillary micropipette in an alternative embodiment of the present invention.
Figure 7:
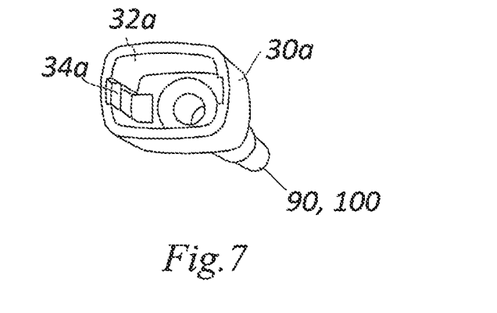
FIG. 7 is a top perspective view and FIG. 7A is a top view, respectively, of the capillary micropipette shown in FIG. 6, with the piston removed.
Figure 7A:
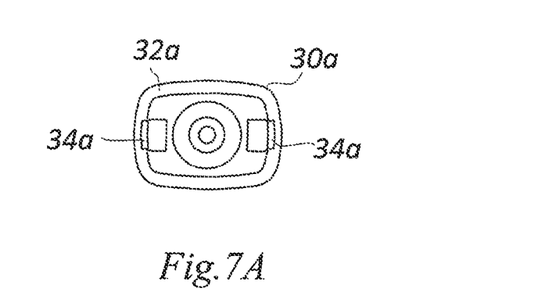
Figure 8:
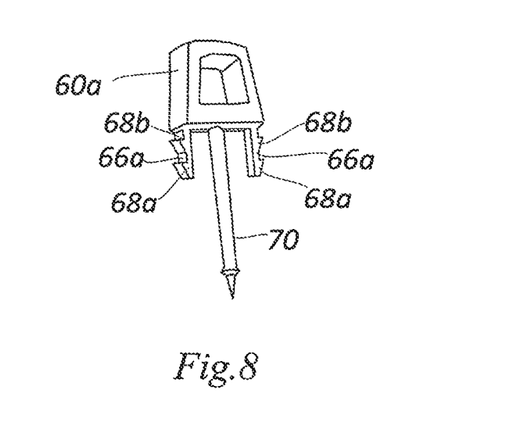
FIG. 8 is a perspective view of the piston of the capillary micropipette shown in FIG. 6.

In the embodiment shown in FIGS. 3-5, the chamber latches 34 and 36 are configured on the chamber wall for snap fit with hooks 68 of cantilever snap fit arms 66 on the push cap. As can be readily understood, such a snap fit configuration can also be arranged in a reversed configuration. For example, in an alternative embodiment shown in FIGS. 6-8, each cantilever snap fit arm 66a of pusher cap 60a includes a lower hook 68a and an upper hook 68b, while upper holding chamber 30a includes only one set of chamber latches 34a on the inner side of chamber wall 32a. Such a reversed configuration also provides a snap fit or cantilever snap joint engagement. With this configuration, in an assembled position lower hooks 68a are already irreversibly snapped over chamber latches 34a, also referred as in a snap-joint position. Once assembled, chamber latches 34a prohibit the push cap from being removed from upper holding chamber 30a, and at the same time, chamber latches 34a inhibit piston rod 70 from moving downward in the absence of a force specifically applied on the push cap. As can be seen in FIG. 6, at the assembled position, upper hooks 68b are situated above and not snapped over or snap jointed with chamber latches 34a. The distance between the lower hook 68a and upper hook 68b is complimentary to the height of chamber latch 34a on chamber wall 32a.

In a further embodiment, the chamber wall may have one set of chamber latches same as those shown in FIG. 6, and each of the cantilever snap fit arms of the push cap may also have one hook same as that shown in FIGS. 3 and 5. In this configuration, as assembled the hooks of the cantilever snap fit arms are situated on top of, and not snapped over, the chamber latches, and the chamber latches inhibit the piston rod from moving downward in the absence of a force specifically applied on the push cap.

As shown in FIGS. 3 and 5, piston rod 70 extends downward from the underside 64 of the push cap and coaxially aligns with tubular member 40 and central opening 38 on the bottom of upper holding chamber 30, and piston head 72 is partly disposed in central opening 38. As can be seen in FIGS. 3 and 5, piston head 72 has a circumferential rim 74 that has an outer diameter complementary to the inner diameter of proximal section 44 of tubular member 40 (see FIG. 11 also). When rim 74 of the piston head moves into tubular member 40 during the use of the device, it prohibits air communication between the spaces above and below rim 74. The axial position of the piston head as described hereinafter refers to the position of its rim 74 unless specified otherwise. Furthermore, in the embodiment shown in FIG. 3, piston head 72 has a conical distal end, which together with the cone shape of central opening 38 facilitates alignment and axial movement of the piston head in the central opening 38 of the upper holding chamber.

When a force is applied thereon, push cap 60 of the piston is movable downward in the upper holding chamber 30, which causes an axial movement of piston head 72. The extent of the movement of push cap 60 is restricted at specific positions in upper holding chamber 30, which results in the axial movement of piston head 72 among distinct axial positions relative to tubular member 40.

Figures 9, 10:
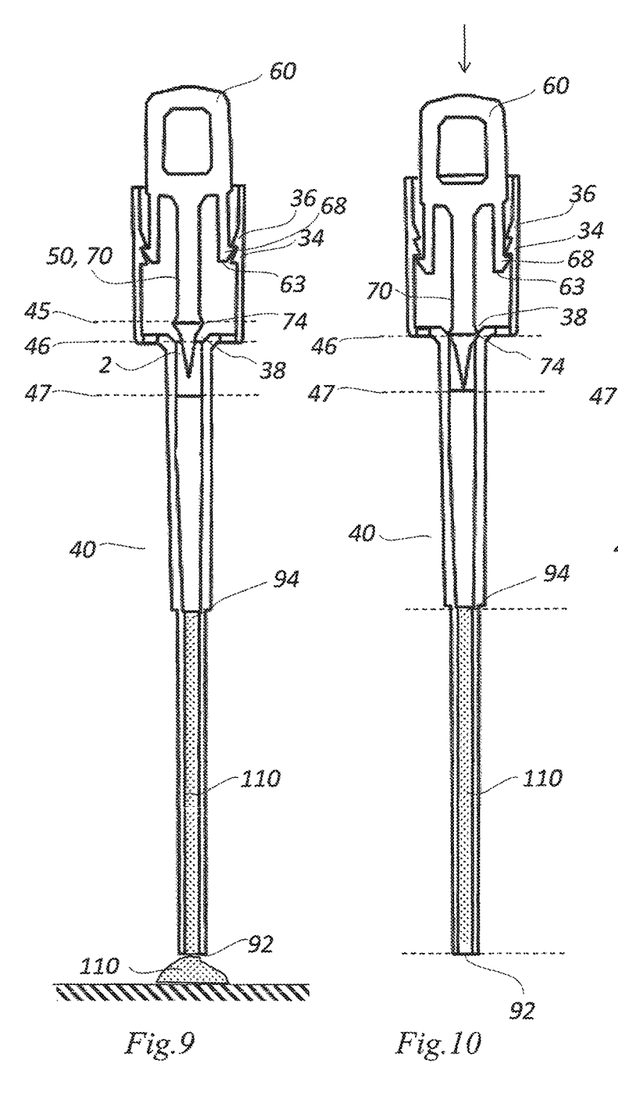
FIG. 9 is an illustrative cross sectional view of the capillary micropipette shown in FIGS. 1 and 3 with the piston in the venting position, in which the cross-sectional hatching is removed for visual clarity.
FIG. 10 is an illustrative cross sectional view of the capillary micropipette shown FIGS. 1 and 3 with the piston in the displacement starting position, in which the cross-sectional hatching is removed for visual clarity.

More specifically, at the assembled position of capillary micropipette 10 before use, as well as at the beginning of transferring and dispensing of a liquid, as shown in FIGS. 3 and 9, hooks 68 of cantilever snap fit arms 66 situate between the lower and upper chamber latches 34 and 36, and rest on top of the lower chamber latches 34. As shown in FIG. 9, at this assembled position, rim 74 of the piston head is disposed at line 45 above central opening 38 on bottom 35 of upper holding chamber 30, and there is a venting space 2 between piston head 72 and central opening 38, which permits air communication between the interior of tubular member 40 and atmosphere through upper holding chamber 30, since the upper holding chamber is open to the atmosphere, not air sealed. Therefore, this position of the piston is referred to as a venting position, and line 45 as indicated is also referred to as venting line. As shown in FIG. 9, the venting position is controlled by lower chamber latches 34 on the chamber wall of upper holding chamber 30, which restricts the piston from moving downward.

As shown in FIG. 10, when push cap 60 is pressed downward (see the arrow) by a user during the use of the device for dispensing a liquid as described hereinafter, hooks 68 of the cantilever snap fit arms snap over the lower chamber latches 34 on the chamber wall first, and the push cap moves further downward under the force. Once rim 74 of the piston head reaches line 46 immediately below central opening 38 on the bottom 35 of upper holding chamber 30, rim 74 seals tubular member 40 and prohibits air communication between tubular member 40 and upper holding chamber 30. As such, further downward movement of push cap 60 causes a downward displacement of a volume of air in tubular member 40. Therefore, the position of the piston as indicated by line 46 is referred to as a displacement starting position, and line 46 is also referred to as displacement starting line.

Figure 11:
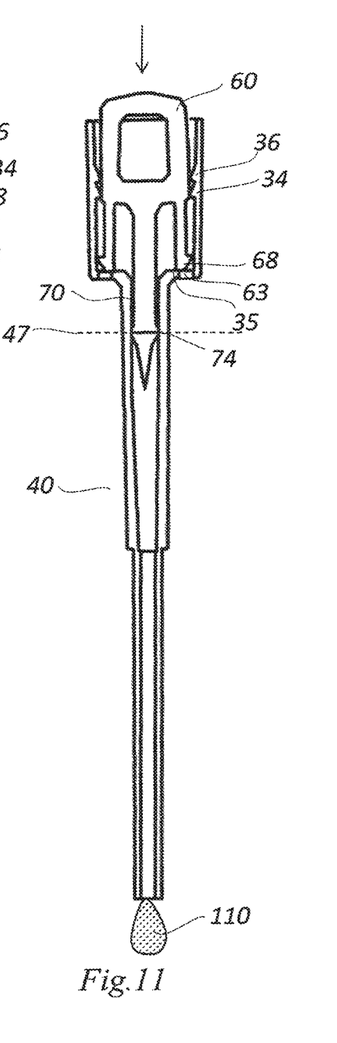
FIG. 11 is an illustrative cross sectional view of the capillary micropipette shown FIGS. 1 and 3 with the piston in the displacement ending position, in which the cross-sectional hatching is removed for visual clarity.

As further shown in FIG. 11, when push cap 60 is pressed downward until the bottoms 63 of cantilever snap fit arms 66 are directly against bottom 35 of holding chamber 30, rim 74 of the piston head reaches the position as indicated by line 47 in tubular member 40. This is the lowest point that rim 74 of the piston head can reach in tubular member 40, therefore, this position of the piston is referred to as a displacement ending position, and line 47 is also referred to as displacement ending line. As shown in FIG. 11, the displacement ending position is controlled by restriction of the piston movement by the structural relationship between the push cap and the upper holding chamber. In this embodiment, bottom 35 of the upper holding chamber functions as a piston stop, and the abutment of bottoms 63 of the snap fit arms of the push cap against bottom 35 of the upper holding chamber prohibits further downward movement of piston head 72 in tubular member 40.

The interior of proximal segment 44 of tubular member 40 is cylindrical. The outer diameter of rim 74 of the piston head has a mating relationship with the inner diameter of proximal segment 44 of the tubular member. The proximal segment 44 has a defined tubular volume between the displacement starting line 46 and the displacement ending line 47. The movement of piston head 72 with its rim 74 from line 46 to line 47 displaces this defined tubular volume of air that is initially contained in the space between the displacement starting and ending lines, which causes dispensing a defined volume of a liquid in the capillary tube 90, as further described hereinafter.

In some embodiments, distal segment 42 of the tubular member may taper downward toward capillary tube 90. In the embodiment shown in FIGS. 3 and 3A, distal segment 42 of the tubular member is integrally connected to capillary tube 90, which forms a single piece structure, as produced through plastic molding. In some other embodiments, capillary tube 90 may be at least partly affixed inside the distal segment 42 as further described hereinafter.

Figure 2:
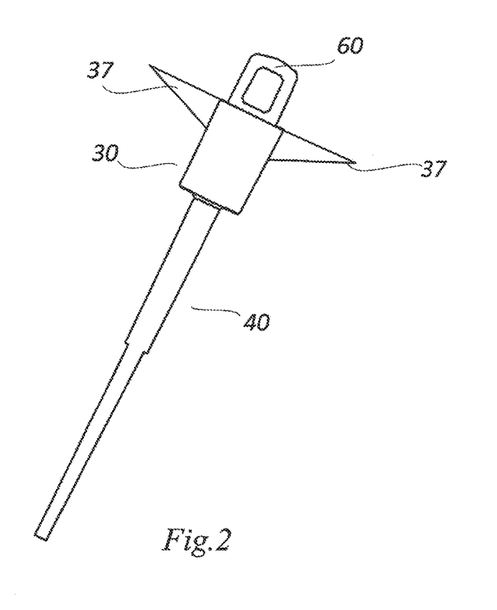
FIG. 2 is a side view of the capillary micropipette in an alternative embodiment.

Optionally, upper holding chamber 30 further includes one or more vertical grooves to guide the movement of push cap 60 in the upper holding chamber. In the embodiment shown in FIGS. 3 and 4, upper holding chamber 30 has two vertical grooves 39 disposed opposing each other. The cantilever snap fit arms 66 and hooks 68 thereon are complementary with grooves 39, and slide along grooves 39 when push cap 60 is pressed downward. Furthermore, optionally upper holding chamber 30 has a pair of through-holes 33 on bottom 35 underneath vertical grooves 39. Through-holes 33 provide an access for formation of chamber latches 34 and 36 as well as the grooves during the manufacture of the device. As further shown in FIG. 2, upper holding chamber 30 may optionally further comprises two outer flanges 37 as a gripping means for the user.

Figures 16, 17, 17A, 18, 20:
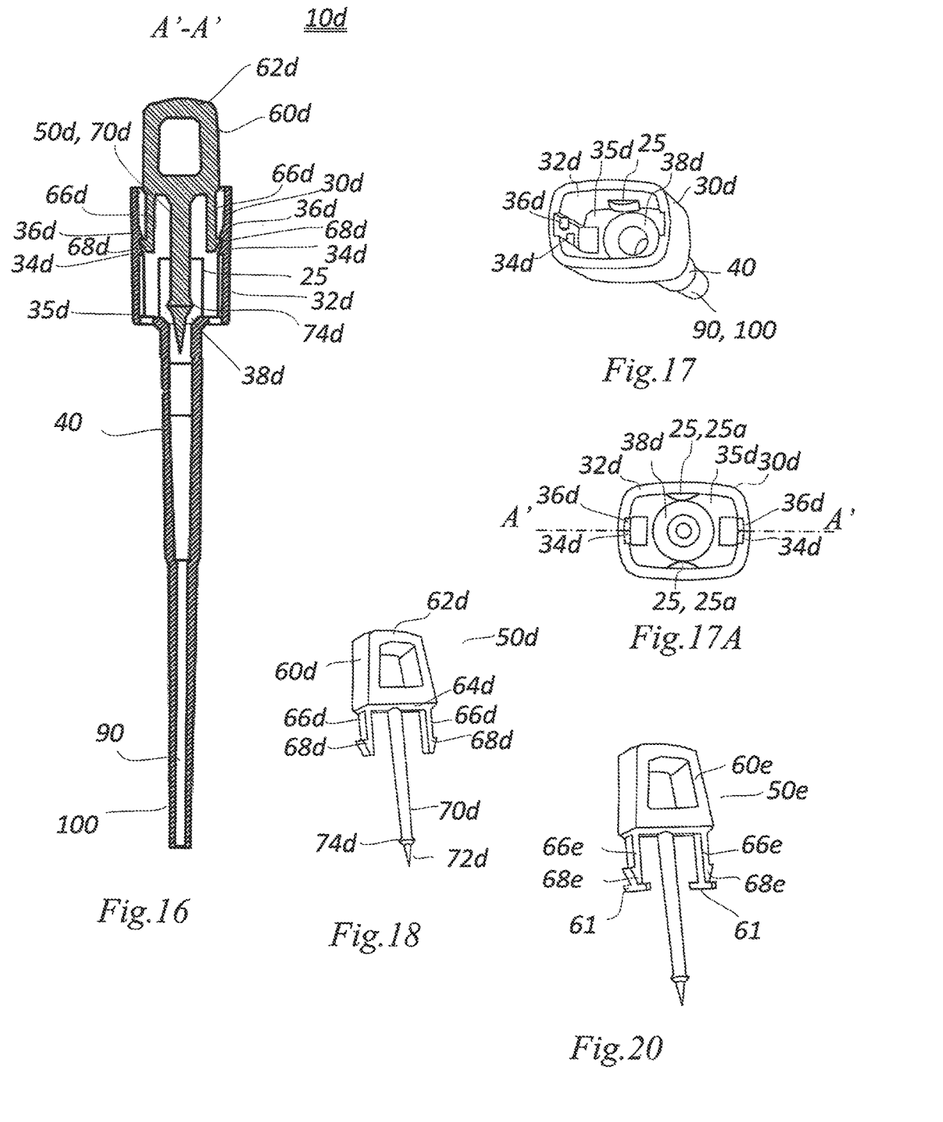
FIG. 16 is a cross sectional view of the capillary micropipette in a further embodiment of the present invention, along line A'-A' in FIG. 17A, with the piston at the venting position.
FIG. 17 is a top perspective view and FIG. 17A is a top view, respectively, of the capillary micropipette shown in FIG. 16, with the piston removed.
FIG. 18 is a perspective view of the piston of the capillary micropipette shown in FIG. 16.
FIG. 20 is a perspective view of a piston of the capillary micropipette in an alternative embodiment.

As described above, in the embodiment shown in FIG. 3 the bottom of the upper holding chamber functions as a piston stop, which controls the displacement ending position of the piston. Alternatively, other forms of piston stop(s) can be provided, wherein abutment of at least one part of the push cap with the piston stop(s) in the upper holding chamber controls the displacement ending position of the piston. In an alternative embodiment as shown in FIGS. 16-18, capillary micropipette 10d includes an upper holding chamber 30d with a central opening 38d on bottom 35d of the upper holding chamber and a tubular member 40d extending downward from the central opening 38d, with the same structural features of capillary micropipette 10 described above in FIGS. 3-4A. Different from the embodiment shown in FIG. 3, in capillary micropipette 10d the upper holding chamber 30d further includes a pair of piston stops 25 disposed on opposing sides of the upper chamber holder, transverse to the direction of chamber latches 34d, 36d. In the embodiment shown, each piston stop 25 is in a form of an elongated element protruding upward from bottom 35d of upper holding chamber 30d. Alternatively, the piston stop may protrude from the chamber wall 32d, without contact with bottom 35d of the upper holding chamber. Moreover, the piston stop may assume other shapes or forms as well as other positions in the upper holding chamber, so long as it inhibits the extent of vertical movement of the push cap in the upper holding chamber to control the displacement ending position of the piston.

Figure 19:
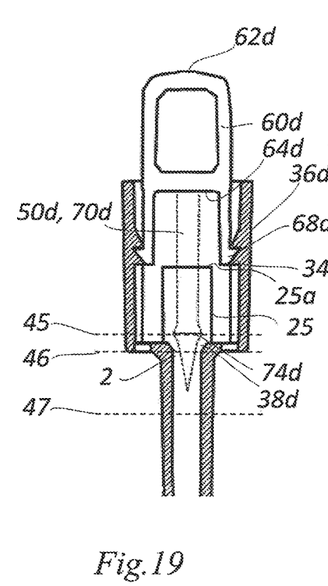
FIGS. 19-19B are enlarged partial cross sectional views of the capillary micropipette shown in FIG. 16, illustrating engagements of the arm snap fit elements of the push cap with the chamber snap fit elements of the upper holding chamber when the piston is at the venting position and displacement starting position, respectively, and the abutment of the push cap with the piston stops when the piston is at the displacement ending position, wherein the piston rod is in phantom for visual clarity of the piston stop.
Figure 19A:
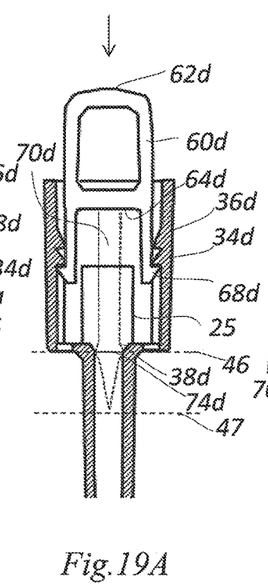
Figure 19B:
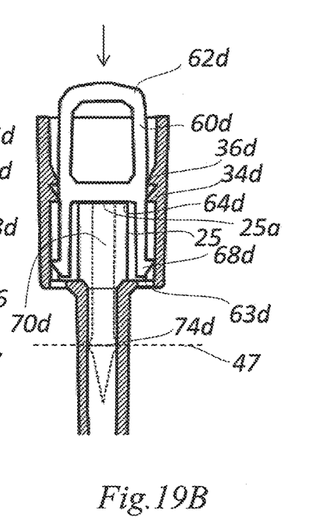

The structural features of capillary micropipette 10d that control the venting position, displacement starting and ending positions of the piston 50d are further illustrated in FIGS. 19 thru 19B in which the piston rod is shown in phantom for visual clarity of relevant elements. FIG. 19 shows the venting position of piston 50d, same as that described above in reference to capillary micropipette 10, at which venting space 2 between piston head 72d and central opening 38d of the upper holding chamber permits air communication between the tubular member 40 and the upper holding chamber 30d. As shown, hooks 68d of snap fit arms 66d are situated on top of the lower set chamber latches 34d on the inner side of chamber wall 32d, and lower set chamber latches 34d inhibit piston rod 70d from moving downward, in the absence of a force specifically applied on push cap 60d.

FIG. 19A shows the displacement starting position of piston 50d, same as that described above in reference to capillary micropipette 10. As shown, hooks 68d are snapped over the lower set chamber latches 34d when top pusher 62d is pressed down by the user (see arrow). FIG. 19B shows the displacement ending position of piston 50d. As shown, after hooks 68d snap over the lower set chamber latches 34d, push cap 60d further moves downward in response to the force applied by the user until the underside 64d of top pusher 62d abuts against the upper end 25a of piston stops 25 in upper holding chamber 30d, which prohibits further downward movement of push cap 60d. At this point, piston 50d reaches its displacement ending position at which rim 74d of piston head 72d is located at line 47, as described above. As can be appreciated, in this embodiment displacement ending position of piston 50d is controlled by the abutment between the underside 64d of top pusher 62d of the push cap and piston stops 25, and the lower ends 63d of snap fit arms 66d may not contact with the bottom of the upper holding chamber 30d at any time during the use of the device.

FIG. 20 shows a further alternative embodiment of a piston 50e that has a push cap 60e, which can be used with the upper holding chamber 30 of capillary micropipette 10 shown in FIGS. 3-4A. As shown in FIG. 20, push cap 60e has two cantilever snap fit arms 66e and each has a hook 68e with the same structure of hooks 68 described above. Moreover, in this embodiment push cap 60e further includes a horizontal bar 61 at the lower end of each snap fit arm 66e. Horizontal bar 61 has a length beyond the width of through-holes 33 in the direction transverse to line A-A in FIG. 4A. In this embodiment, the bottom 35 of the upper holding chamber 30 functions as a piston stop, similar to that described in the embodiment shown in FIG. 3. During the use of the capillary micropipette as described above, push cap 60e is pressed down by the user until the horizontal bars 61 abut against the bottom 35 of the upper holding chamber on both sides of through-holes 33, which establishes the displacement ending position of piston 50e.

Figure 13:
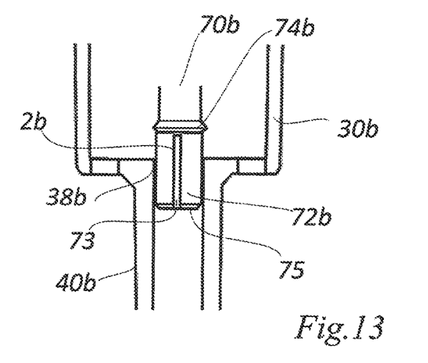
FIG. 13 is a partial cross sectional view of the capillary micropipette in a further alternative embodiment of the present invention.

FIG. 13 further illustrates the structure of the piston head in an alternative embodiment. As shown, piston head 72b has a general cylindrical shape, and central opening 38b on the bottom of upper holding chamber 30b is straight without tapering. In this embodiment, piston head 72b has a venting recess 73 extending from immediately underneath rim 74b to distal end 75 of piston head 72b. The space 2b in the venting recess 73 is the venting space between the piston head and the central opening. At the venting position shown in FIG. 13, air communication between tubular member 40b and atmosphere (through upper holding chamber 30b) is established through space 2b in the venting recess 73.

Returning to FIG. 3, as further shown capillary tube 90 has a proximal open end 94 connected to distal segment of tubular member 40 and a distal open end 92 which is sufficiently blunt to prevent injury to a user. In some embodiments, the inner diameter of capillary tube 90 can be from about 0.2 to about 3 millimeters, depending on the volume of a liquid to be dispensed. The total internal volume of capillary tube 90 can be from 1 microliter (μl) to 250 microliters. The inner diameter of capillary tube 90 is smaller than the inner diameter of distal segment of tubular member 40, and the ratio of the inner diameter of distal segment 42 of tubular member 40 to the inner diameter of capillary tube 90 can be from about 1.5 to about 3.5. In some embodiments, proximal open end 94 of capillary tube 90 forms an inner upper edge 95 free of contact with the inner wall of tubular member 40, as shown in FIG. 3A. Because of a sudden substantial increase in diameter at the interface between the tubular member and the capillary tube, the capillary action induced by capillary tube 90 stops at its proximal open end naturally. Alternatively, a liquid-tight filter block can be placed on the proximal open end of the capillary tube. When the liquid reaches the liquid-tight filter block, aspiration stops.

The interior surface of capillary tube 90 is wettable. In some embodiments, capillary tube 90 can be made of a wettable thermoplastic acrylonitrile barrier resin, a polyether block polyamide, cellulose acetate propionate or butyrate, and other water wettable thermoplastic polymers. In one example, a thermoplastic acrylonitrile barrier resin under the trade name BAREX™ can be used. In another example, a polyether block polyamide under the trade name PEBAX™ can be used. Alternatively, capillary tube 90 can also be made from other plastics, glass, metals or ceramics.

In some embodiments, capillary tube 90 can be made of polystyrene, polypropylene, acrylics, polyvinylchloride, polycarbonate and other polymers with a pretreated interior surface. These materials are hydrophobic, however, suitable surface treatments can be used to render the surface hydrophilic. These treatment processes are well known to those skilled in the art. For examples, addition of polyethylene glycol or surfactant(s) to the molding resins for extrusion or molding of the capillary tubes, subjecting the surfaces to plasma treatment to cause hydrophilic functional groups to be incorporated onto the surface of the molded parts, treatment of the molded part with a strong liquid oxidizing agent or other similar processes can be used for the purpose of the present invention. Moreover, corona discharge, flame treatment, coating of the tube with surfactant(s) and coating of the capillary tube with protein can also be used to pretreat the inner surface of the capillary tube. The capillary micropipette is commonly used for transfer and dispense of blood samples, and the material used for surface treatment, particularly the surfactants, are preferably non-hemolytic.

In some embodiments, the interior surface of capillary tube 90 may be coated with a hydrophilic polymer, such as alkylamine ethoxylate, polyacrylamides, poly(N-vinyl lactams), poly(ethylene oxide), poly(propylene oxide), cellulosics, polyacrylic acids, polyvinyl alcohols, and polyvinyl ethers. In some embodiments, the interior surface of capillary tube 90 may be coated with a hydrophilic coating that comprises a polyacrylate or polymethacrylate polymer matrix associated with a hydrophilic polymer selected from the group consisting of poly(N-vinyl lactams), poly(ethylene oxide), poly(propylene oxide), polyacrylamides, cellulosics, polyacrylic acids, polyvinyl alcohols, and polyvinyl ethers, as disclosed in U.S. Pat. No. 6,866,936 which is incorporated by reference in its entirety. In another embodiment, the hydrophilic coating may comprise a polyurethane polymer matrix associated with an above mentioned hydrophilic polymer as disclosed in U.S. Pat. No. 6,238,799 which is incorporated by reference in its entirety.

In some embodiments, the interior surface of capillary tube 90 may be coated using an aqueous coating composition to render the surface hydrophilic, for example using the composition disclosed in U.S. Pat. No. 7,008,979 which is incorporated by reference in its entirety. Such aqueous coating composition comprises a modified polyurethane carrier dispersed or emulsified in water; a hydrophilic water-soluble organic monomer, oligomer, prepolymer, polymer or copolymer derived from N-vinylpyrrolidone; aqueous colloidal metal oxide; and a crosslinker. The colloidal metal oxide includes aluminate, silicate, titanate, zincate, stannate, argentite, aluminum silicate, aluminum titanate, zirconate, zircoaluminate, or a combination thereof. The crosslinker includes aziridine, carbodiimide, oxirane, alcohol, glycydyl ether, glycidyl ester, carboxyl acid, amine, epoxide, vinyl sulfone, amide, allyl compound and related hardener, their prepolymeric resins or a combination thereof.

Preferably, the capillary tube is transparent or translucent, which permits the user to observe aspiration of the liquid, as well as to monitor whether any air bubble enters the capillary tube during aspiration. In some embodiments, the same plastic material can be used for the capillary tube 90, the tubular member 40, as well as the upper holding chamber 30. These three components can form a single piece integral structure by plastic molding, as illustrated in the embodiment shown in FIG. 3. Moreover, the push cap and piston rod can also be made of plastics by plastic molding, and the push cap, piston rod and piston head including the rim may have a single piece integral structure, as shown in FIG. 5.

Figure 14:
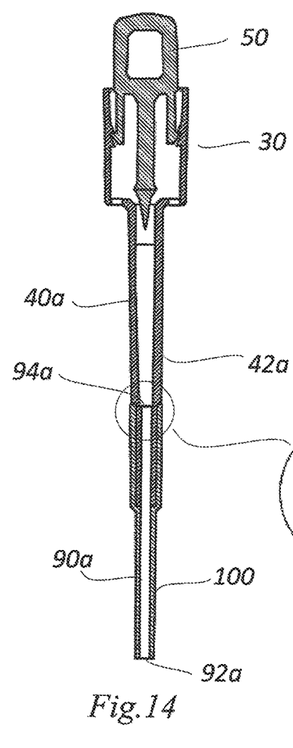
FIG. 14 is a cross sectional view of the capillary micropipette in one embodiment of the present invention.

In some embodiments, capillary tube can be made of glass. As shown in FIG. 14, different from a plastic molded single piece structure shown in FIG. 3, proximal open end 94a of a glass capillary tube 90a is affixed inside distal segment 42a of tubular member 40a. As further shown in FIG. 14A, the upper edge 95a of proximal open end 94a is free of contact with tubular member 40a. Such a sudden substantial increase in diameter at the interface between the capillary tube and the tubular member, as described above, facilitates stop of aspiration by capillary action when blood or other liquid samples reaches the proximal open end.

Figure 14A:
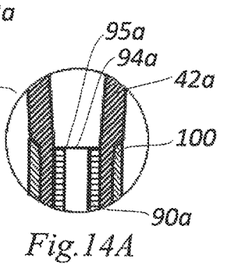
FIG. 14A is an enlarged partial cross sectional view showing the structure between the proximal open end of the capillary tube and distal segment of the tubular member of the capillary micropipette shown in FIG. 14.

The exterior of glass capillary tube 90a is covered by a plastic material to protect the glass capillary tube. In some embodiments as shown in FIGS. 14 and 14A, glass capillary tube 90a is covered by a heat shrink plastic tubing 100, from distal open end 92a to the lower portion of distal segment 42a of tubular member 40a. The heat shrink plastic tubing 100 attaches tightly to the exterior of glass capillary tube 90a after a heating assembly process. The heat shrink plastic tubing protects glass capillary tube 90a from breakage during transportation and use, and further ensures distal open end 92a to be blunt.

Figure 15:
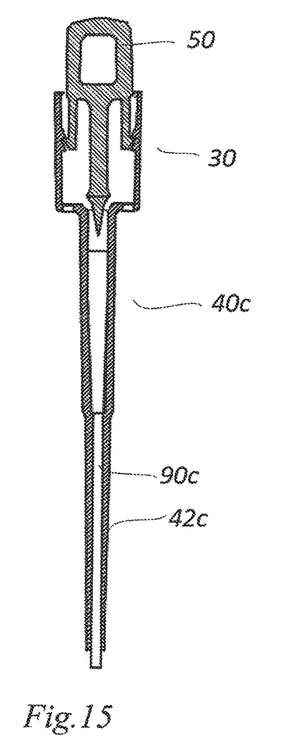
FIG. 15 is a cross sectional view of the capillary micropipette in a further embodiment of the present invention.

In an alternative embodiment as shown in FIG. 15, distal segment 42c of tubular member 40c extends substantially to the distal open end of glass capillary tube 90c. The glass capillary tube 90c can be affixed to the inside of tubular member 40c by press fit or by an adhesive.

In embodiments shown in FIGS. 14-15, glass capillary tube 90a and 90c provides superior capillary action in aspirating biological samples such as blood, plasma, and the like. On the other hand, the exterior of the capillary tube is protected by a plastic material, which protects the thin glass tube from breaking, and hence provides enhanced safety to the users in handling biological samples. Moreover, the glass tube, the heat shrink plastic tubing, and the molded tubular member can be transparent or translucent.

FIGS. 9 thru 11 illustrate the use of capillary micropipette 10 shown in FIG. 3 in transferring a blood from an open site, such as a blood from a fingerstick, and dispensing of a defined volume of the blood to a destination, for example to a "point-of-care" cassette, a microscope slide, or the like.

FIG. 9 illustrates the first step of transferring and dispensing of a blood sample. The single use capillary micropipette assembled by the manufacturer is used directly by the user. As shown, the piston 50 of the assembled capillary micropipette 10 is at its venting position described above, with rim 74 of the piston head 72 situated at venting line 45. The distal open end 92 of capillary tube 90 is immersed in a blood 110 from a fingerstick by the user. The blood is aspirated into capillary tube 90 driven by capillary action, and the aspiration stops when the blood reaches the proximal open end 94, as described above. During the aspiration, air inside tubular member 40 above the aspirated blood is vented through the venting space 2 between central opening 38 on the bottom of upper holding chamber 30 and the piston head, therefore, no pressure builds up within tubular member 40 to inhibit aspiration. When the blood reaches the proximal open end 94 of the capillary tube, where the aspiration stops, and the distal open end 92 of capillary tube 90 is moved away from the fingerstick blood by the user.

Then, the user positions the distal open end 92 of the capillary micropipette to a designated location, such as at a sample inlet of a cassette or on top of a microscope slide, then press on top of push cap 60 to dispense the blood. As shown in FIG. 10, when push cap 60 is pressed down, it causes hooks 68 of cantilever snap fit arms 66 to snap over the lower chamber latches 34 on the chamber wall, and rim 74 of the piston head to reach the displacement starting position, as indicated by line 46 shown in FIG. 10. As described above, further downward movement of the push cap due to the force applied thereon causes displacement of air contained in the proximal segment 44 of tubular member 40. As shown in FIG. 11, when the bottoms 63 of the cantilever snap fit arms reach the bottom 35 of upper holding chamber 30, the push cap completely stops, and at this time rim 74 of the piston head reaches the displacement ending position of the piston as indicated by line 47 in FIG. 11. At this point, the tubular volume of air between lines 46 and 47 is displaced downward, which causes the capillary micropipette to dispense a defined volume of the blood.

In some embodiments, the total internal volume of capillary tube 90 can be larger than the defined tubular volume between lines 46 and 47 of tubular member 40. As such, after dispense, a residue of the aspirated blood remains in the tip of capillary tube 90. As can be appreciated, with this configuration the dispensed blood volume is controlled by the defined tubular volume between lines 46 and 47 of tubular member 40, and the dispensed blood volume is the same as the defined tubular volume. This configuration is particularly advantageous for applications where the accuracy and precision of the dispensed sample volume are required. Sometimes unskilled user may position the capillary tube improperly and cause aspiration beyond the capillary tube. With this configuration, the dispensed blood with the defined volume is not affected by the additional filling of the blood during aspiration. Moreover, this configuration is advantageous for dispensing a blood sample substantially free of air bubbles, because the residue of the blood remaining at the tip of the capillary tube has an effect of preventing air in the capillary micropipette from mixing into the dispensed blood.

Furthermore, in some embodiments the total internal volume of capillary tube 90 is equal to the defined tubular volume between lines 46 and 47 in the proximal segment 44 of tubular member 40. When rim 74 of the piston head reaches the displacement ending position as described above, the aspirated blood is dispensed completely and the dispensed blood volume is equal to the defined tubular volume. In a further alternative embodiment, the total internal volume of capillary tube 90 can be smaller than the defined tubular volume between lines 46 and 47 of tubular member 40. With this configuration, the dispended blood volume is the total internal volume of the capillary tube.

It has been found that the capillary micropipette of the present invention enables delivery of a defined volume of blood accurately and consistently. The dispense volume of the capillary micropipette can be from 1 µl to 250 µl.

As can be appreciated, capillary micropipette 10 is a single use device. As described above, during the dispense process hooks 68 of the cantilever snap fit arms snap over the lower chamber latches 34 in response to the force applied on the push cap. This is a one way and irreversible movement. Once hooks 68 snap over the lower chamber latches 34, the venting space 2 is no longer available for venting which would be required if one tries to use the same micropipette again for aspiration by capillary action. Moreover, because of the irreversible snap joint mechanism, the push cap is locked in the upper holding chamber and the piston in a used device cannot be taken out from the capillary micropipette. This is particularly advantageous in handling infectious disease samples, as well as in situations where cross contamination is a concern.

Capillary micropipette of the present invention can be used for various applications where manual transferring and dispensing of a defined volume of a liquid sample from an open site, such as from a fingerstick blood or an open specimen container, are needed. The capillary micropipette is particularly suitable for providing a defined volume of blood or other biological samples for point-of-care diagnostic tests, such as for QuickRead diagnostic instruments from Orion Diagnostica, and other point-of-care instruments.

Moreover, the capillary micropipette can be used for dispensing blood for preparing blood smears on microscope slides, particularly suitable from a fingerstick blood. In preparing a blood smear on a microscope slide, any air bubble in a blood sample dispensed on the slide can cause a disturbing bubble, and the slide has to be discarded and a replacement blood smear has to be prepared. Therefore, a dispensed blood sample free of air bubble is particularly advantageous. As described above in reference to some embodiments, using the capillary micropipette of the present invention the dispensed blood can be essentially free of air bubbles, as such the number of blood smears can be effectively reduced due to elimination of redundant preparation caused by air bubbles.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A single use capillary micropipette for dispensing a defined volume of a liquid, the capillary micropipette comprising:
    (a) a housing comprising
    an upper holding chamber having an open top, a chamber wall having at least one set of chamber snap fit elements on an inner side thereof, one or more piston stops, and a bottom with a central opening; and
    a tubular member extending downward from the central opening on the bottom of the upper holding chamber;
    (b) a piston comprising
    a push cap disposed at least partially in the upper holding chamber, the push cap including a top pusher and at least one set of snap fit arms extending downward from an underside of the top pusher; each of the at least one set of snap fit arms comprising at least one hook complementary to a corresponding chamber snap fit element; and in an assembled position of the capillary micropipette the at least one hook on each of the at least one set of snap fit arms being situated on top of corresponding chamber snap fit element; and
    a piston rod having a piston head at a distal end thereof, the piston rod extending downward from the underside of the top pusher, coaxial with the central opening on the bottom of the upper holding chamber and the tubular member; in the assembled position of the capillary micropipette, a venting space between the piston head and the central opening on the bottom of the upper holding chamber permitting air communication between the tubular member and atmosphere through the upper holding chamber; and
    (c) a capillary tube having a proximal open end connected to the tubular member and an opposing distal open end; the capillary tube capable of aspirating a liquid through the distal open end by capillary action to the proximal open end thereof while the capillary micropipette permitting venting through the venting space during aspiration;
    the push cap movable downward in response to a force applied thereon to an extent at which at least one part of the push cap abuts against the one or more piston stops of the upper holding chamber, and downward movement of the push cap causing the at least one hook on each of the snap fit arms of the push cap to irreversibly snap over corresponding chamber snap fit element and the piston head to slide in the tubular member in the absence of venting thereby resulting in dispensing a defined volume of the liquid aspirated in the capillary tube.

2. The capillary micropipette of claim 1, wherein the chamber sidewall further comprises a second set of chamber snap fit elements on the inner side thereof disposed above the at least one set of chamber snap fit elements and complementary to the hooks of the at least one set of snap fit arms of the push cap; and in the assembled position of the capillary micropipette the hooks on the at least one set of snap fit arms are irreversibly snapped over the second set of chamber snap fit elements.

3. The capillary micropipette of claim 1, wherein each of the at least one set of snap fit arms further comprises a second hook disposed below the at least one hook and complementary to the corresponding chamber snap fit element; and in the assembled position of the capillary micropipette the second hooks on the snap fit arms are irreversibly snapped over the at least one set of chamber snap fit elements.

4. The capillary micropipette of claim 1, wherein a proximal segment of the tubular member has a defined tubular volume between a displacement starting position and a displacement ending position of the piston.

5. The capillary micropipette of claim 4, wherein at the displacement starting position of the piston, the piston head is disposed immediately underneath the central opening of the upper holding chamber, and the piston head seals the tubular member from air communication with the upper holding chamber.

6. The capillary micropipette of claim 4, wherein at the displacement ending position of the piston, at least one part of the push cap abuts against the one or more piston stops in the upper holding chamber, thereby prohibiting further advance of the piston rod in the tubular member.

7. The capillary micropipette of claim 4, wherein an outer diameter of a circumferential rim of the piston head has a mating relationship with an inner diameter of the proximal segment of the tubular member.

8. The capillary micropipette of claim 4, wherein a total internal volume of the capillary tube is equal to the defined tubular volume in the proximal segment of the tubular member.

9. The capillary micropipette of claim 4, wherein a total internal volume of the capillary tube is larger than the defined tubular volume in the proximal segment of the tubular member.

10. The capillary micropipette of claim 4, wherein a total internal volume of the capillary tube is smaller than the defined tubular volume in the proximal segment of the tubular member.

11. The capillary micropipette of claim 1, wherein an inner diameter of a distal segment of the tubular member is larger than an inner diameter of the capillary tube.

12. The capillary micropipette of claim 11, wherein a ratio of the inner diameter of the distal segment of the tubular member to the inner diameter of the capillary tube is from about 1.5 to about 3.5.

13. The capillary micropipette of claim 1, wherein the capillary tube is made of a water wettable thermoplastic polymer, glass, ceramics, or metal.

14. The capillary micropipette of claim 1, wherein the capillary tube is made of a plastic and an interior surface of the capillary tube is pretreated such that the interior surface is rendered wettable.

15. The capillary micropipette of claim 1, wherein the capillary tube is made of glass and an exterior of the capillary tube is covered by a heat shrink plastic tubing.

16. The capillary micropipette of claim 1, wherein the upper holding chamber further includes one or more vertical grooves on the inner side of the chamber wall, and the snap fit arms are configured to move long the vertical grooves.

17. The capillary micropipette of claim 1, wherein the central opening on the bottom of the upper holding chamber has a general cone shape and the piston head is tapered.

18. A method of transferring a liquid and dispensing a defined volume of the liquid using a single use capillary micropipette, the method comprising:
(a) providing a capillary micropipette comprising:
a housing comprising an upper holding chamber having an open top, a chamber wall having at least one set of chamber snap fit elements on an inner side thereof, one or more piston stops, and a bottom with a central opening; and a tubular member extending downward from the central opening on the bottom of the upper holding chamber;
(ii) a piston comprising a push cap disposed at least partially in the upper holding chamber, the push cap including a top pusher and at least one set of snap fit arms extending downward from an underside of the top pusher; each of the at least one set of snap fit arms comprising at least one hook complementary to a corresponding chamber snap fit element; and in an assembled position of the capillary micropipette the at least one hook on each of the at least one set of snap fit arms being situated on top of corresponding chamber snap fit element; and a piston rod having a piston head at a distal end thereof, the piston rod extending downward from the underside of the top pusher, coaxial with the central opening on the bottom of the upper holding chamber and the tubular member; in an assembled position of the capillary micropipette, a venting space between the piston head and the central opening on the bottom of the upper holding chamber permitting air communication between the tubular member and atmosphere through the upper holding chamber; and
(iii) a capillary tube having a proximal open end connected to the tubular member and an opposing distal open end; and
(b) immersing the distal open end of the capillary tube in the liquid, and allowing the liquid to be aspirated into the capillary tube by capillary action while the capillary micropipette permits venting through the venting space during aspiration;
(c) removing the distal open end of the capillary tube from the liquid when the liquid is aspirated to the proximal open end of the capillary tube; and
(d) pressing on top of the push cap to cause the hooks of the at least one set of snap fit arms to irreversibly snap over the at least one set of chamber snap fit elements of the upper holding chamber and to move the push cap downward until the at least one part of the push cap abuts against the one or more piston stops in the upper holding chamber, thereby the piston head sliding in the tubular member in the absence of venting and resulting in dispensing a defined volume of the liquid aspirated in the capillary tube.

19. The method of claim 18, wherein the method further comprises discarding the capillary micropipette after dispensing the defined volume of the liquid, with the piston locked in the housing of the capillary micropipette by snap joint engagement between the at least one set of snap fit arms of the push cap and the at least one set of chamber snap fit elements in the upper holding chamber.

20. The method of claim 18, wherein the liquid to be transferred is on an open site or in an open container.

* * * * *